(12) United States Patent
Loxley et al.

(10) Patent No.: US 6,711,234 B1
(45) Date of Patent: Mar. 23, 2004

(54) X-RAY FLUORESCENCE APPARATUS

(75) Inventors: Neil Loxley, Durham (GB); David Keith Bowen, Denver, CO (US); Ladislav Pina, Prague (CZ)

(73) Assignee: Bede Scientific Instruments Limited, Bowburn (GB)

( * ) Notice: Subject to any disclaimer, the term of this patent is extended or adjusted under 35 U.S.C. 154(b) by 92 days.

(21) Appl. No.: 10/130,586
(22) PCT Filed: Nov. 23, 2000
(86) PCT No.: PCT/GB00/04452
§ 371 (c)(1), (2), (4) Date: May 16, 2002
(87) PCT Pub. No.: WO01/38861
PCT Pub. Date: May 31, 2001

(30) Foreign Application Priority Data

Nov. 23, 1999 (GB) ................................................ 9927555

(51) Int. Cl.$^7$ ................................................ G21K 1/06
(52) U.S. Cl. ................................................ 378/145; 378/85
(58) Field of Search ................................ 378/145–150, 378/84, 85

(56) References Cited

FOREIGN PATENT DOCUMENTS

| CH | 318890 | 1/1957 |
| EP | 318012 | 5/1989 |
| EP | 943914 | 9/1999 |

OTHER PUBLICATIONS

Hunter, W.R., et al.; *A Grating Crystal Monchromator for the Spectral Range 5 EV to 5KEV*, Nuclear instruments & Methods in Physics Research, North–Holland Publishing Co., Amsterdam, NL.; vol. 915, No. 1/2.; Apr. 1, 1982; pp. 141–153.

Voss. J, et al.: *Grazing Incidence Optics for Soft X–Ray Microscopy*; Review of Scientific Instruments; American Institute of Physics; New York, New York, U.S.; vol. 63, No. 1 PT 2A, 1992, pp. 569–573.

*Primary Examiner*—Craig E. Church
(74) *Attorney, Agent, or Firm*—Blackwell Sanders Peper Martin, LLP

(57) ABSTRACT

This invention relates to a portable apparatus for carrying out X-ray fluorescence spectrometry on specimen materials at a distance from the apparatus. The apparatus comprises an X-ray generating tube, such as a microfocus tube, and two paraboloidal X-ray reflecting mirrors. The first collecting mirror is positioned in close coupled arrangement adjacent to the exit window of the tube, such that it emits parallel X-ray radiation to the second focusing mirror, which is aligned on the axis of and spaced apart from the first mirror (11). The second mirror (12) collects the parallel X-ray radiation at its end closest to the first mirror and emits X-ray radiation in a focused beam onto the specimen. The distance between the first and second mirrors is adjusted to suit the distance from the X-ray tube to the specimen. Focal spots on the specimen of diameter less than 15 microns (590.55 microinches) are possible, enabling precise analysis of small areas of the specimen.

19 Claims, 2 Drawing Sheets

X-RAY FLUORESCENCE APPARATUS

APPLICATION CROSS-REFERENCES

This application claims priority of International Application No. PCT/GB00/04452 filed Nov. 23, 2000 and published in English. This application also claims priority of Great Britain Patent No. 9927555.4, filed Nov. 23, 1999.

TECHNICAL FIELD

This invention relates to an apparatus and method for carrying out X-ray fluorescence spectrometry (XRF), and particularly to a portable apparatus, which is able to generate X-ray fluorescence in materials at a distance from the apparatus.

BACKGROUND OF THE INVENTION

X-ray fluorescence spectrometry is a non-destructive technique for determining the elemental composition of a wide variety of materials. X-ray fluorescence (XRF) is the secondary emission of X-rays at wavelengths characteristic of each element present when a material is irradiated with a primary X-ray beam. In commercially available XRF spectrometers, the bulk sample is usually irradiated directly by X-rays from a sealed tube. The technique is sufficiently sensitive to detect elements which are present at concentrations as low as one or two parts per million. There is, however, a requirement for greater sensitivity in applications in which it is desired to examine small areas on bulk samples or where the sample itself is small. The type of instrumentation required for this technique is sometimes called Micro X-ray Fluorescence Analysis (MXRFA or MXA) apparatus.

Several methods presently exist for MXRFA. Among them is the use of mono-capillary and poly-capillary X-ray focusing optics coupled to standard or microfocus X-ray generating tubes. These suffer from the drawback that samples have to be placed very close to the output of the optic (generally less than 300 microns (11,811.02 microinches). The minimum focal spot generally commercially available with polycapillaries is 28 microns (1,102.36 microinches). This is relatively large and limits the fineness of the resolution with which areas of a sample can be analyzed.

Another method, which presently exists for MXRFA is to use a synchrotron in conjunction with Fresnel lenses. Such apparatus is massive and not portable, although beams having a focal spot of only 1 microns (39.37 microinches) can be achieved, giving greater accuracy in analysis of samples. This method suffers from the disadvantage that synchrotron radiation sources are large fixed facilities, which are not portable and are not available in most laboratories, so cannot be accessed on a routine basis.

A further method of MXRFA, which exists is the use of a synchrotron in conjunction with mono-capillary lenses. Such apparatus is also not portable, and beam sizes are limited to a focal spot of 5 microns (196.85 microinches)–10 microns (393.70 microinches).

SUMMARY OF THE INVENTION

It is therefore an object of the invention to provide an apparatus for carrying out X-ray fluorescence spectrometry which is portable yet which is capable of analyzing samples of less than 30 microns (1,181.10 microinches).

According to a first aspect of the present invention there is provided an apparatus for carrying out X-ray fluorescence spectrometry comprising an X-ray generating tube and two paraboloidal X-ray reflecting mirrors, the generating tube having an X-ray source and an X-ray exit window through which X-ray radiation from said source is emitted, the first mirror being aligned on a first axis and positioned in close coupled arrangement adjacent to the exit window, the second mirror being aligned on said first axis and being positioned in spaced apart relationship to the first mirror, the first mirror being adapted to collect diverging X-ray radiation at its first end adjacent to the collecting window and to emit X-ray radiation in a substantially parallel beam at its second end, the second mirror being adapted to collect substantially parallel X-ray radiation at its first end closest to the first mirror and to emit X-ray radiation in a focused beam at its second end.

By using first and second mirrors in this way, the focal spot on the target of the X-ray tube is transferred to the image plane, at unity magnification. The focal spot at the image plane on the sample subjected to fluorescence has a high brightness, and focal spots on the sample of diameter less than 15 microns (590.55 microinches) are possible.

Preferably the first and second mirrors are cylindrical specularly reflecting mirrors. Preferably the first end of the first mirror is positioned between 5 millimeters (0.20 inches) and 50 millimeters (1.97 inches) from the X-ray source.

Preferably the apparatus further comprises a housing containing the first and the second mirrors.

The second mirror may be fixed in position relative to the first mirror.

Alternatively the second mirror may be movable in position relative to the first mirror. The apparatus may further comprise a guide means for guiding the second mirror in a direction parallel to the first axis, and adjustment means for adjusting the spacing of the first and the second mirrors.

The apparatus may further comprise angular adjustment means adapted to allow angular adjustment of the mirror housing with the X-ray generator tube.

Preferably the X-ray generator tube is adapted to produce an X-ray source at the target having a maximum width of less than 50 microns (1,968.50 microinches), more preferably less than 15 microns (590.55 microinches).

According to a second aspect of the present invention there is provided a method of delivering X-ray radiation to a specimen for the purpose of X-ray fluorescence spectrometry using an X-ray generating tube, the generating tube having an X-ray exit window through which X-ray radiation is emitted, the method comprising placing first and second paraboloidal X-ray reflecting mirrors between the exit window and the specimen, using the first mirror to collect diverging X-ray radiation at its first end adjacent to the exit window and to emit X-ray radiation in a substantially parallel beam at its second end, and using the second mirror to collect substantially parallel X-ray radiation at its first end closest to the first mirror and to emit X-ray radiation at its second end to a focused spot on the specimen.

Preferably, the method uses an apparatus according to the first aspect of the invention.

BRIEF DESCRIPTION OF THE DRAWINGS

Embodiments of the invention will now be described, by way of example only, with reference to the accompanying figures, where.

DETAILED DESCRIPTION OF THE INVENTION

Figure 1:
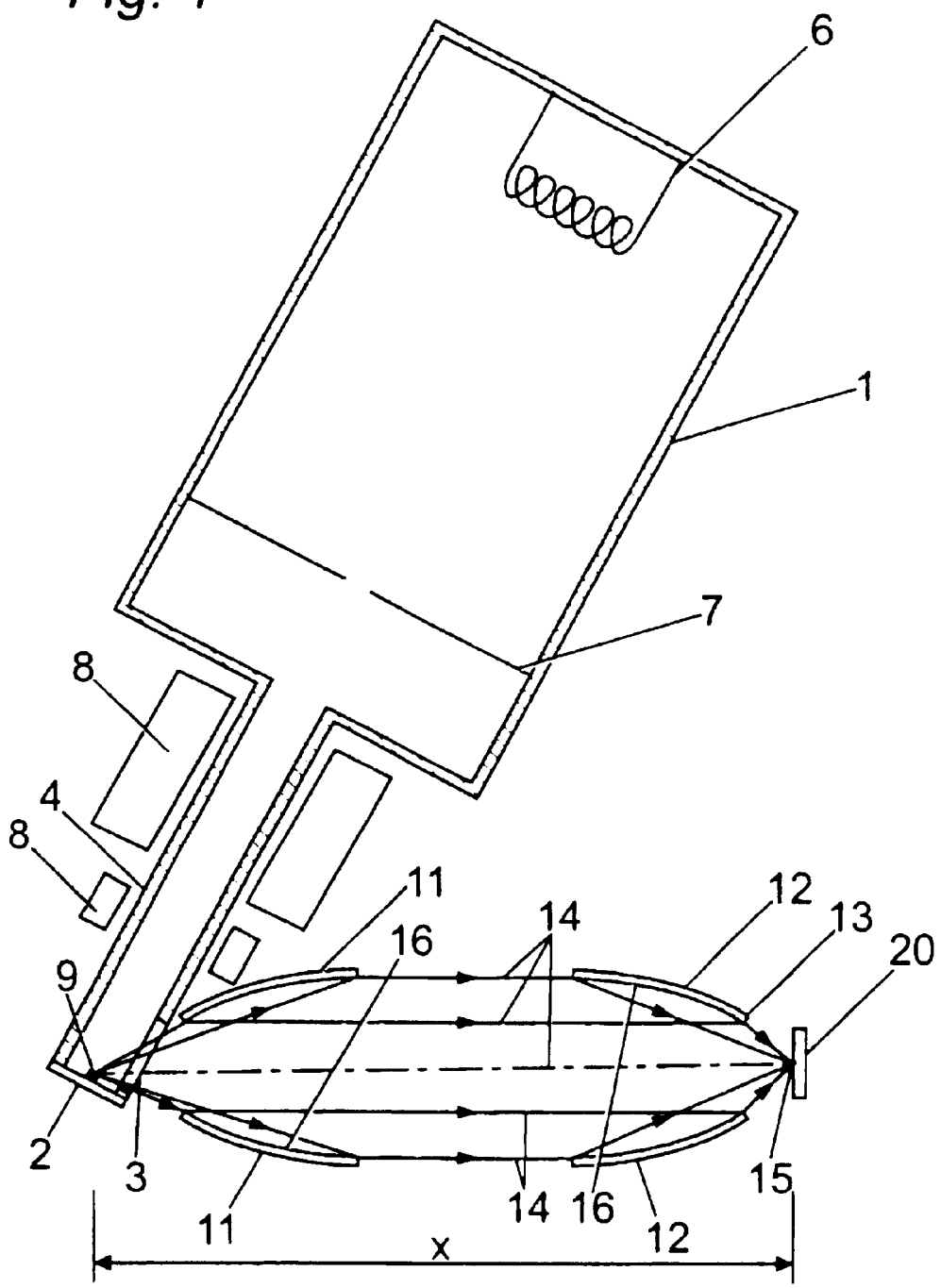
FIG. 1 is a schematic view of two X-ray focusing mirrors used in accordance with the invention to focus an X-ray beam from the source on the X-ray target to the sample to be subject to X-ray fluorescence spectrometry.

Referring to FIG. 1 there is shown, in a schematic form and not to scale, an X-ray generating tube 1 having an exit window 3, an electron source 6, an anode 7, focusing and stigmator coils 8 and a target 2 on which is formed an X-ray source 9. A suitable X-ray generating tube is the MICROSOURCE™ tube described in International Patent Application No PCT/GB97/02022, which is a compact X-ray generator capable of producing small-size, high intensity X-ray sources for low power input. Typically the exit window 3 of the generator 1 is provided in the narrow portion 4 of the X-ray tube about which the X-ray focusing coils 8 are arranged, to the side of the X-ray target 2. A first X-ray focusing mirror 11, the collection mirror, is positioned adjacent to the exit window 3 in close coupled arrangement, and a second X-ray focusing mirror 12, the focusing mirror, is arranged coaxially with the first X-ray focusing mirror 11, to transfer the x-ray radiation to a spot on a specimen 20. Suitable mirrors 11, 12 are MICROMIRROR™ X-ray optics as supplied by Bede Scientific Instruments Ltd. The mirrors are cylindrical specularly reflecting mirrors. Each mirror comprises a cylindrical body having an axially symmetrical passage extending therethrough. There is an aperture at each end of the body, which communicates with the passage. The reflecting surface is on the inside of the long axis of the cylinder and has a shape corresponding to a paraboloid of revolution about the long axis of the cylinder.

A paraboloidal profile produces an almost parallel, essentially non-divergent beam 14. The interior reflecting surface 16 is coated in an exceptionally smooth coating of gold or similar in order to provide specular reflectivity. Typically the mirror is made of nickel and is of the order of 10 millimeters (0.39 inches) to 100 millimeters (3.94 inches) in length, typically about 30 millimeters (1.18 inches). The outside diameter of the mirror is typically 6 millimeters (0.24 inches). The internal diameter is typically less than 4 millimeters (0.16 inches). The entry aperture is generally smaller than the exit aperture.

The two mirrors have an identical profile. The source to first mirror distance is in the range 5 millimeters (0.20 inches) to 50 millimeters (1.97 inches).

Typically the X-ray generator produces a sub-15 microns (590.55 microinches) spot source on a target of less than 10 millimeters (0.39 inches) diameter at a power of up to 30 W.

The first mirror or paraboloidal optic 11 has a high angle of collection and reflects X-rays into a substantially parallel beam. In practice a beam of divergence less than 40 arc seconds can be achieved.

The second mirror or paraboloidal optic 12 takes the parallel beam and focuses it down to a spot 15 on the specimen 20 of a size similar to that of the X-ray source, typically a spot with a diameter of less than 15 microns (590.55 microinches).

The focus 15 of the second optic 12 is typically about 10 millimeters (0.39 inches) to 20 millimeters (0.79 inches) away from the far end 13 of optic, giving a much more convenient working distance than is available from prior art XRF apparatus, such as monocapillaries.

The distance between the two optics 11, 12 may be continuously changed without affecting the focal spot quality, thereby allowing a range of source to sample distances X to be achieved. Typically distance X will be 100 millimeters (3.94 inches) or more.

X-ray optics have very well defined profiles and low surface roughness, and therefore work at very high efficiency. By using paraboloidal mirrors the apparatus of the invention achieves broad band transmission of X-rays, with an efficiency close to 1, since only double reflection of the X-ray radiation is required.

The invention achieves high X-ray brightness at the focal plane on the target, with a focal spot diameter of as low as 10 microns (393.70 microinches).

The apparatus of the invention is truly portable, giving it applications in areas such as forgery detection, which require the apparatus to be taken to the specimen.

A parabolic surface will produce a parallel beam if the source is placed at the focal point. Conversely a focused beam will be brought to a focus when a parabolic surface is illuminated with a parallel beam. Therefore the method and apparatus of the invention serves to transfer the image of the X-ray spot from the target to the specimen. It should be noted that the target may not be perpendicular to the axis of the mirrors, so that the effective dimension of the image on the target, when viewed along the axis of the mirrors, is less than the actual dimension on the target.

The focal spot size at the specimen is thus primarily determined by the spot size on the target of the X-ray tube. Since the first mirror produces a parallel beam, the focal spot size at the specimen is, within practical limits, independent of the distance of the second mirror along the beam axis. Therefore the second mirror can be placed at the required distance from the first in order to suit the geometrical requirements of the equipment.

Figure 2:
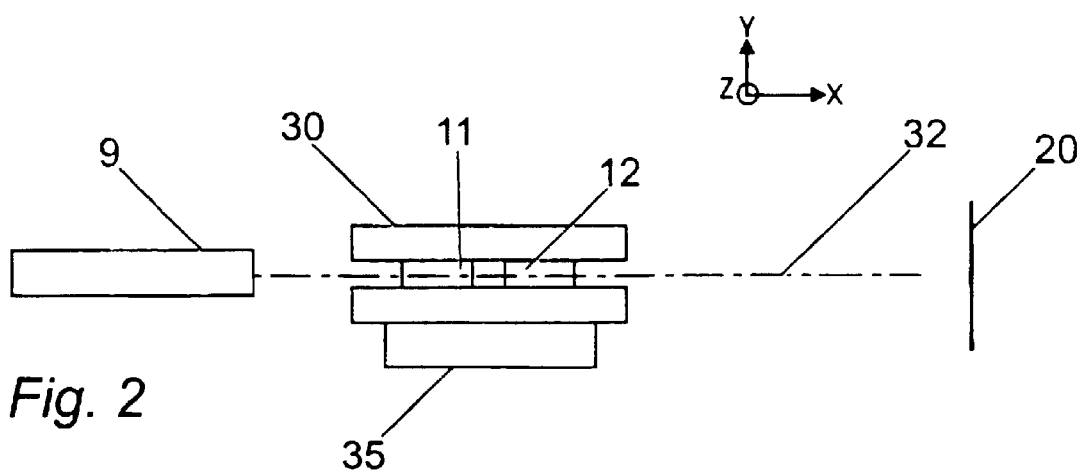
FIG. 2 is a schematic view of an apparatus according to a first aspect of the invention having mirrors fixed relative to each other.
Figure 3:
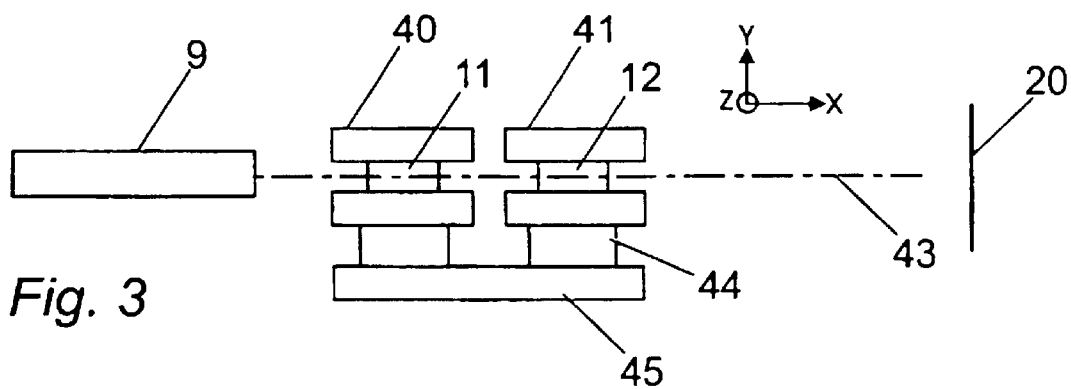
FIG. 3 is a schematic view of an apparatus according to a second aspect of the invention having mirrors adjustable relative to each other.

FIGS. 2 and 3 show two schematic arrangements for housing the apparatus of the invention.

In the simplest case, shown in FIG. 2, the collector and focusing mirrors 11, 12 are aligned with each other and are fixed within a cylindrical housing 30. The housing is aligned relative to the X-ray source 9, shown purely schematically in FIGS. 2 and 3, on the beam axis 32, either fixedly or adjustably. The housing 30 may be subject to a partial or total vacuum, to improve the efficiency of the mirrors and reduce energy absorption as the X-rays pass through the gas in the housing 30. It is to be understood that in practice the source 9 is part of an X-ray generating tube 1 (not shown in FIGS. 2 and 3).

In use the housing 30 is placed adjacent to the X-ray source, and a control mechanism 35 allows fine adjustment of the position of the housing 30 in the x, y and z directions so that the axis 32 of the mirrors is accurately aligned with the X-ray source 9 and directed to the specimen 20. The control mechanism 35 may comprise any suitable mechanisms, which permit fine translational adjustment, such as lead screws or Vernier controls.

In the example of FIG. 3, each mirror 11, 12 is provided with a separate housing 40, 41. The housings 40, 41 may further be contained in an outer housing, not shown, which may be partially or completely evacuated. The apparatus allows alignment of the second mirror 12 relative to the first mirror 11 and translation of the second mirror 12 along the beam axis 43 by means of control mechanism 44.

Alignment of the whole mirror assembly relative to the X-ray source 9 is possible by means of control mechanism 45. Mechanisms 44 and 45 are similar to mechanism 35 described with reference to FIG. 2, and are not described further.

Although the invention has been described with reference to a microfocus X-ray generator, the invention can be used with any suitable X-ray generator, which is capable of producing a small source of sufficient intensity.

The mirror housing 30,40 may be attached to the X-ray tube 1 or may be positioned independently.

These and other modifications and improvements can be incorporated without departing from the scope of the invention.

What is claimed is:

1. An apparatus for carrying out X-ray fluorescence spectrometry comprising an X-ray generating tube and two paraboloidal X-ray reflecting mirrors, the generating tube having an X-ray source and an X-ray exit window through which X-ray radiation from said source is emitted, the first mirror being aligned on a first axis and positioned in close coupled arrangement adjacent to the exit window, the second mirror being aligned on said first axis and being positioned in spaced apart relationship to the first mirror, the first mirror being adapted to collect diverging X-ray radiation at its first end adjacent to the collecting window and to emit X-ray radiation in a substantially parallel beam at its second end, the second mirror being adapted to collect substantially parallel X-ray radiation at its first end closest to the first mirror and to emit X-ray radiation in a focused beam at its second end, the mirrors being arranged coaxially along their axis of symmetry, and the mirrors being paraboloids of revolution.

2. An apparatus according to claim 1, wherein the first and second mirrors are cylindrical specularly reflecting mirrors.

3. An apparatus according to claim 1, wherein the first end of the first mirror is positioned between 5 millimeters (0.20 inches) and 50 millimeters (1.97 inches from the X-ray source.

4. An apparatus according to claim 1, wherein the apparatus further includes a housing containing the first mirror and the second mirror.

5. An apparatus according to claim 2, wherein the apparatus further includes a housing containing the first mirror and the second mirror.

6. An apparatus according to claim 1, wherein the second mirror is fixed in position relative to the first mirror.

7. An apparatus according to claim 1, wherein the second mirror is movable in position relative to the first mirror.

8. An apparatus according to claim 6, further including a guide means for guiding said second mirror in a direction parallel to the first axis, and adjustment means for adjusting the spacing of the first mirror and the second mirror.

9. An apparatus according to claim 4, further including an angular adjustment means adapted to allow angular adjustment of the mirror housing with the X-ray generating tube.

10. An apparatus according to claim 1, wherein the X-ray generator tube is adapted to produce an X-ray source at the target having a maximum width of less than 50 microns (1,968.50 microinches).

11. An apparatus according to claim 1, wherein the X-ray generator tube is adapted to produce an X-ray source at the target having a maximum width of less than 15 microns (590.55 microinches).

12. An apparatus according to claim 1, wherein the apparatus is portable and the X-ray generating tube is a microfocus generator.

13. A method of delivering X-ray radiation to a specimen for the purpose of X-ray fluorescence spectrometry using an X-ray generating tube, the X-ray generating tube having an X-ray exit window through which X-ray radiation is emitted, the method comprising placing first and second paraboloidal X-ray reflecting mirrors between the exit window and the specimen, using the first mirror to collect diverging X-ray radiation at its first end adjacent to the exit window and to emit X-ray radiation in a substantially parallel beam at its second end, and using the second mirror to collect substantially parallel X-ray radiation at its first end closest to the first mirror and to emit X-ray radiation at its second end to a focused spot on the specimen, the mirrors being arranged coaxially along their axis of symmetry, and the mirrors being paraboloids of revolution.

14. A method according to claim 13, wherein the first and second mirrors are cylindrical specularly reflecting mirrors.

15. A method according to claim 13, wherein the first end of the first mirror is positioned between 5 millimeters (0.20 inches) and 50 millimeters (1.97 inches from the X-ray source.

16. A method according to claim 14, wherein the first end of the first mirror is positioned between 5 millimeters (0.20 inches) and 50 millimeters (1.97 inches from the X-ray source.

17. A method according to claim 13, wherein the focused spot on the specimen has a maximum dimension of 50 microns (1,968.50 microinches).

18. A method according to claim 13, further including the step of adjusting the spacing of the first mirror and the second mirror to produce a focused spot on the specimen.

19. A method according to claim 13, wherein the X-ray generating tube is a microfocus generator.

* * * * *